United States Patent [19]

Lash

[11] Patent Number: 4,867,176

[45] Date of Patent: Sep. 19, 1989

[54] FEMALE CONDOM

[76] Inventor: Harvey Lash, 2309 Byron St., Palo Alto, Calif. 94301

[21] Appl. No.: 145,399

[22] Filed: Jan. 19, 1988

[51] Int. Cl.$^4$ ............................................. A61F 13/00
[52] U.S. Cl. .................................... 128/830; 128/844; 604/330; 604/349
[58] Field of Search .................... 604/12, 15, 16, 317, 604/327, 328, 329, 330, 331, 346, 347, 348, 349, 350, 351, 352, 353, 11, 13, 14, 17, 18; 128/127–131, 132 R, 138 R, 830, 842–844; 206/398–402, 601, 303

[56] References Cited

U.S. PATENT DOCUMENTS

| | | | |
|---|---|---|---|
| 899,251 | 9/1908 | Graham | 604/330 |
| 2,816,542 | 12/1957 | Freeman | 128/844 |
| 3,136,417 | 6/1964 | Clinch | 604/349 |
| 3,346,883 | 10/1967 | Ersek | 604/352 |
| 4,004,591 | 1/1977 | Freimark | 604/330 |
| 4,148,317 | 4/1979 | Loyer | 604/11 |
| 4,281,648 | 8/1981 | Rogers | 128/132 R |
| 4,284,079 | 8/1981 | Adair | 604/349 |
| 4,304,226 | 12/1981 | Drobish et al. | 128/127 |
| 4,381,771 | 5/1983 | Gabbay | 604/330 |
| 4,648,867 | 3/1987 | Conner et al. | 604/14 |
| 4,735,621 | 4/1988 | Hessel | 604/349 |

FOREIGN PATENT DOCUMENTS 0210413  9/1909  Fed. Rep. of Germany ...... 604/328

OTHER PUBLICATIONS

Outline For Successful Prophylactic Program (Waterbury, CT: The Hemingway Press, 1934, The GeeBee Co. 7–16).

Primary Examiner—C. Fred Rosenbaum
Assistant Examiner—Mario Costantino
Attorney, Agent, or Firm—Harris Zimmerman; Howard Cohen

[57] ABSTRACT

A condom designed for use by females includes an oblong tube formed of a pliant, thin material impervious to spermatozoa and pathogenic organisms, and including a closed distal end. The proximal end is open, and may be provided with a semi-rigid retaining ring secured to the open end to maintain the opening. The proximal portion of the tube is rolled about the retaining ring to reduce the size of the device in a vending package. The invention includes a tampon-like lubricated applicator having a soft, broad tip portion received within the closed distal end, and a tubular handle extending distally therefrom. The applicator is adapted to facilitate vaginal insertion of the condom, with the retaining ring having a sufficient diameter to prevent the proximal end from passing into the vagina. The tubular handle may be provided with a telescoping portion which is collapsed in the vending package and extended to facilitate insertion of the condom, the proximal end portion of the condom being unrolled from the retaining ring sufficiently to provide sufficient length for vaginal insertion and the applicator then being removed. A thickened, resilient cap portion may be provided at the distal end of the condom to aid retention of the condom after insertion. The proximal end of the condom tube can be provided with an adhesive annular seal covered with a releasable protective strip during intercourse and peelable afterwards to expose the adhesive and permit the proximal end to be joined together to prevent spillage.

15 Claims, 4 Drawing Sheets

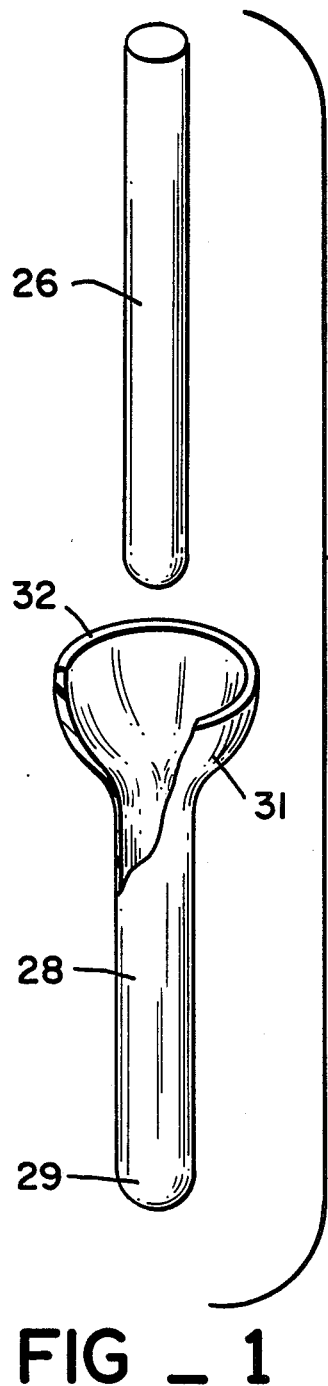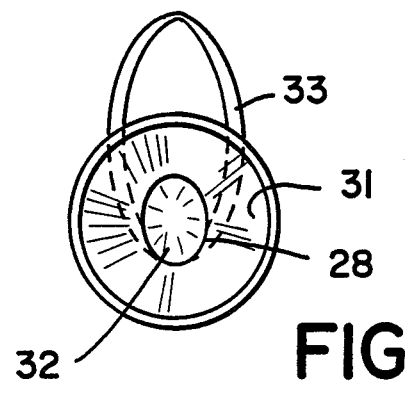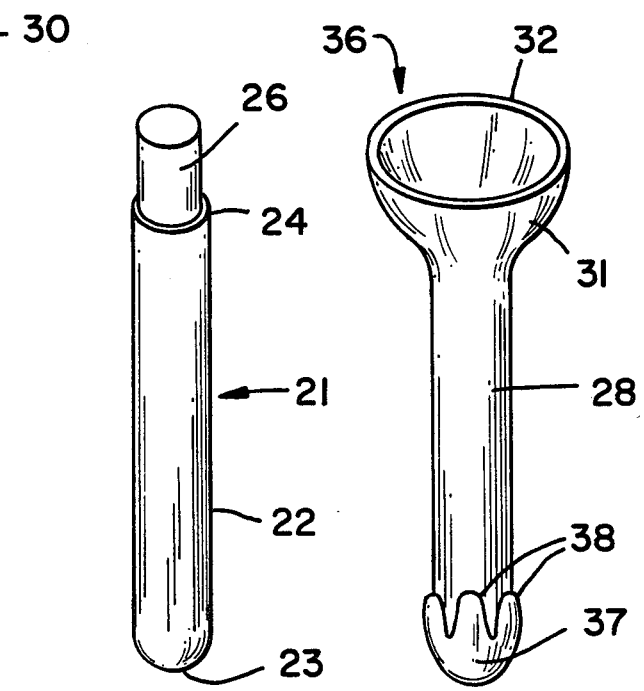

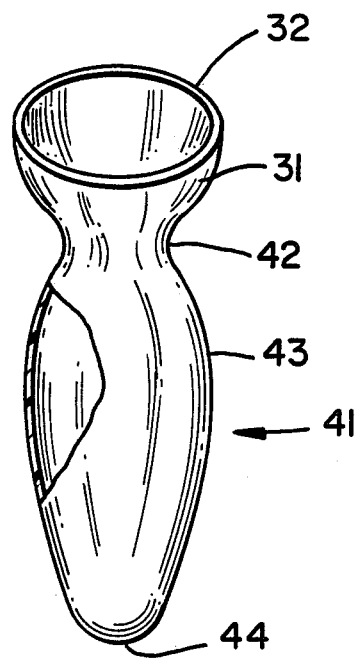
FIG _ 5
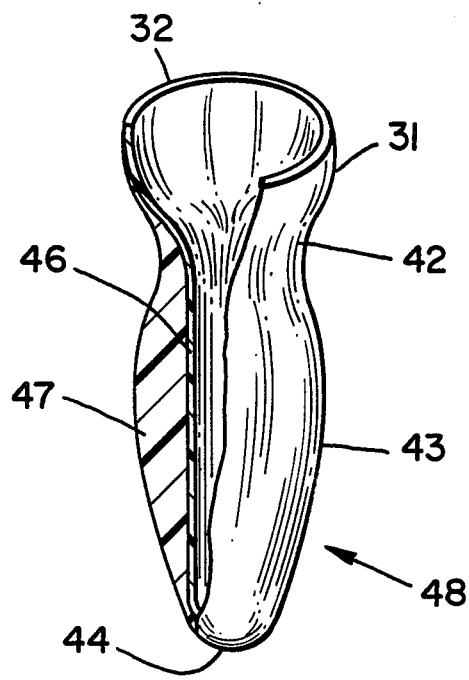
FIG _ 6
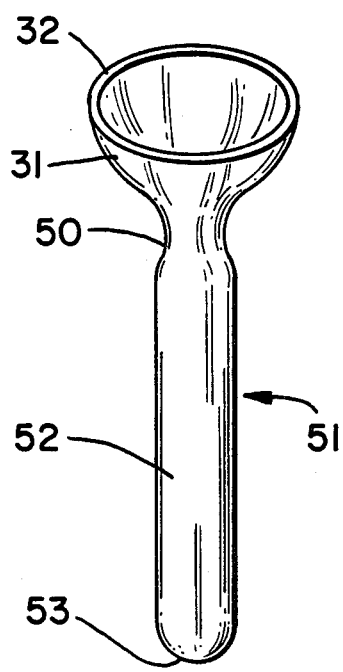
FIG _ 7
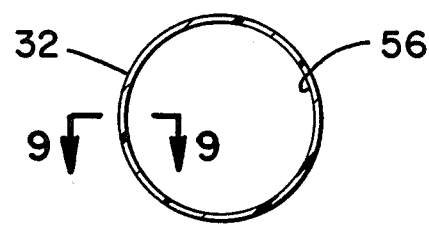
FIG _ 8
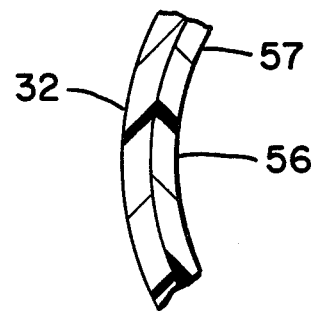
FIG _ 9

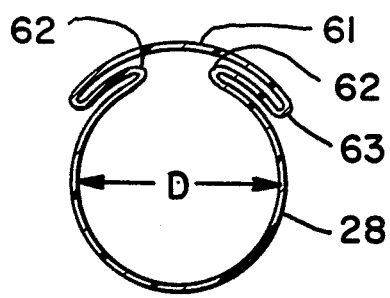
FIG _ 10
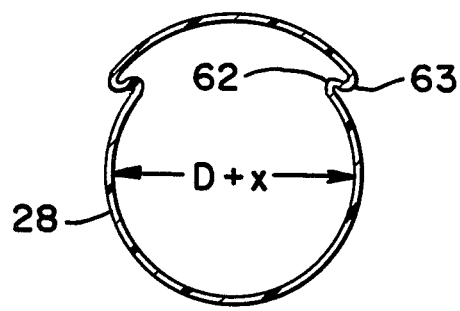
FIG _ 11
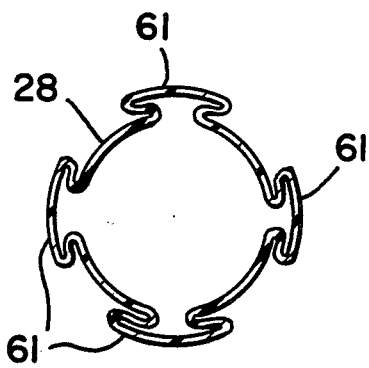
FIG _ 12
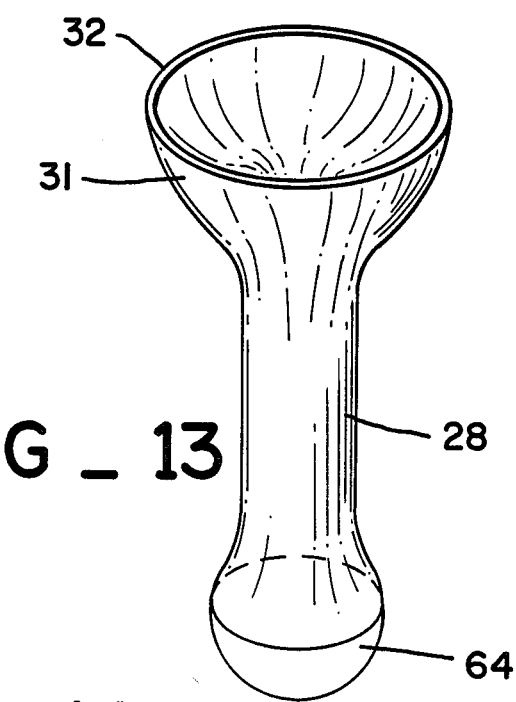
FIG _ 13
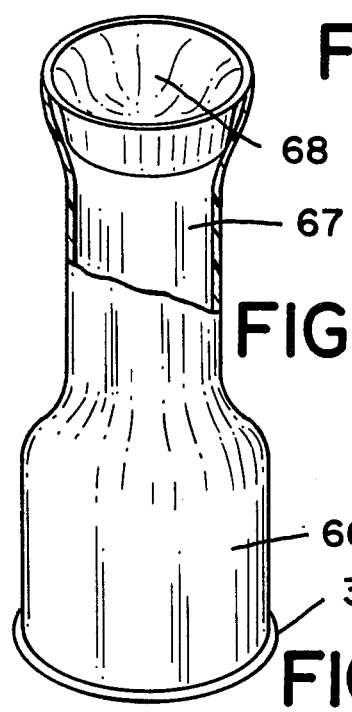
FIG _ 14
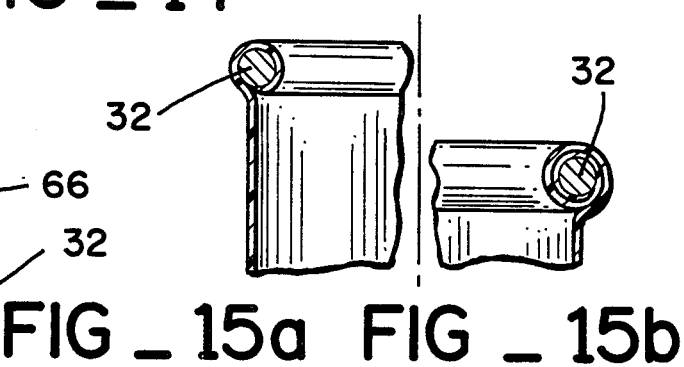
FIG _ 15a  FIG _ 15b

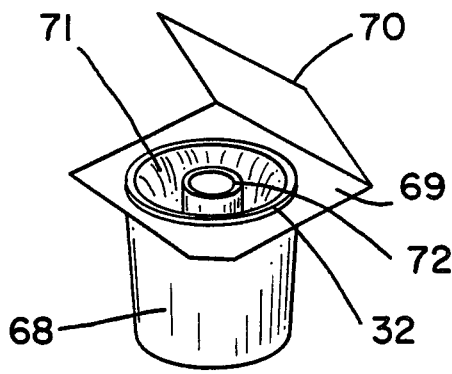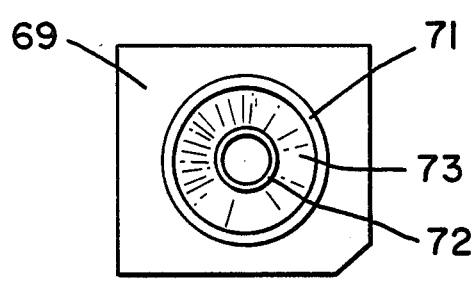
FIG _ 16  FIG _ 17
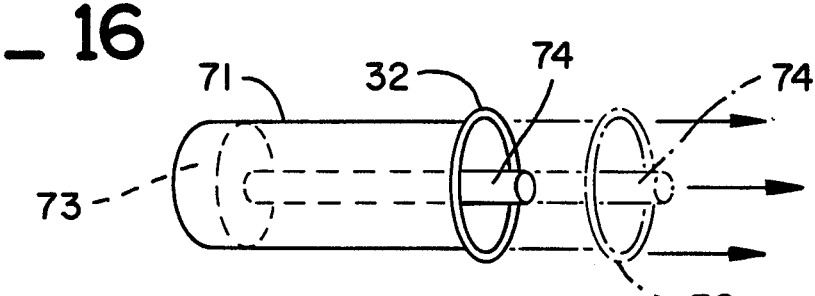
FIG _ 18
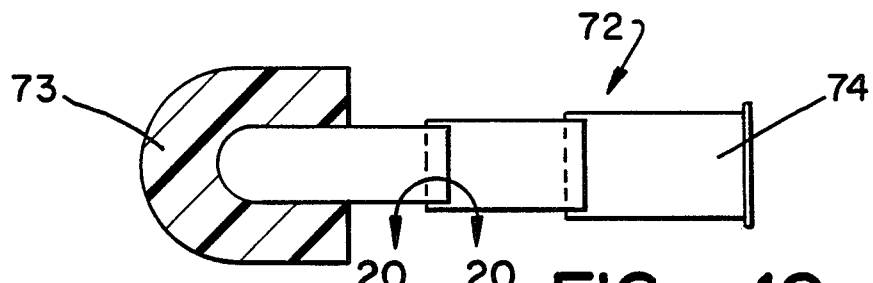
FIG _ 19
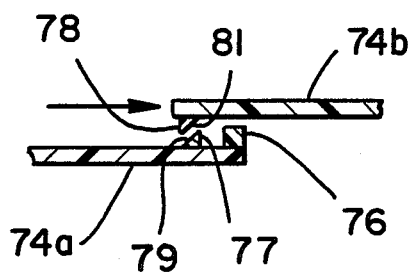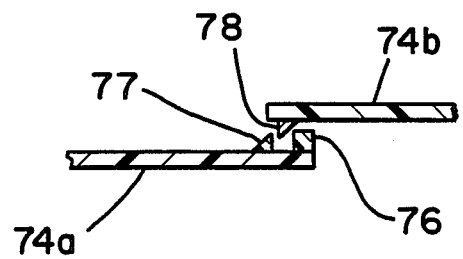
FIG _ 20a  FIG _ 20b

FEMALE CONDOM

BACKGROUND OF THE INVENTION

Among the myriad forms and methods of contraception, the oldest and most prosaic device, the condom, has recently become the subject of intense medical and commercial interest. The complications associated with intrauterine devices and birth control pills have mitigated against their use in most cases. Moreover, the appearance of the HIV virus and the impending Acquired Immune Deficiency Syndrome epidemic have created an atmosphere of caution and prudence in which sexually active adults must consider protecting themselves from infection by HIV virus and other venereal diseases. It is generally accepted as fact that the condom provides the best protection from venereal disease and HIV virus, aside from complete sexual abstinence.

Condoms as known in the prior art are known to suffer some drawbacks, chiefly in that they interfere with the normal progression of intercourse. Use of the condom requires male arousal first, followed by an interruption to open a condom package and apply the condom to the male member. Moreover, condoms are usually packaged in a lubricating fluid, and are often cold to the touch. This application of a cold object to the male member is aversive to many individuals, and discouraging to its use. Furthermore, the membrane of the condom, no matter how pliant or thin, is often viewed as a barrier to the most intimate tactile sensations of intercourse.

From a commercial standpoint, surveys have shown that nearly 50% of condoms purchased are sold to women, although it is clear that condoms as known in the prior art must be worn by the male. Therefore there is an implication that many women are concerned about contraception and disease prevention, and desirous of taking steps toward prevention of both. However, there is no device known in the prior art that prevents conception and disease, and can be used solely by the female prior to intercourse.

SUMMARY OF THE PRESENT INVENTION

The present invention generally comprises a condom adapted to be used solely by a female prior to intercourse. This female condom is designed to overcome the objections to use of prior art male condoms, and to prevent the transmission of disease by precluding skin-to-skin genital contact during intercourse.

The condom designed for use by females includes an oblong tube formed of a pliant, thin material impervious to spermatozoa and pathogenic organisms, and including a closed distal end. The proximal end is open, and joined a semi-rigid retaining ring to maintain the opening. The proximal portion of the tube is rolled about the retaining ring to reduce the length of the device in a vending package. The invention includes a tampon-like lubricated applicator having a soft, broad tip portion adapted to be received within the closed distal end, and a tubular handle extending distally therefrom.

The applicator is adapted to facilitate vaginal insertion of the condom, with the retaining ring having a diameter sufficient to prevent the proximal end from passing into the vagina. The tubular handle may be provided with a telescoping portion which is collapsed in the vending package and extended to facilitate insertion of the condom, the proximal end portion of the condom being unrolled from the retaining ring sufficiently to provide sufficient length for vaginal insertion and the applicator then being removed. In one embodiment a thickened, resilient cap portion may be provided at the distal end of the condom to aid retention of the condom after insertion. In a further embodiment, the sidewall of the condom tube may be provided with one or more pleats extending parallel to the axis of the condom to permit diametrical expansion during intercourse. In another embodiment, a medial portion of the condom tube may be provided with a constriction zone of diminished diameter to engage and be retained about the base of the male penis after intercourse begins. In a further embodiment, the proximal end of the condom tube is provided with an adhesive annular seal covered with a releasable protective strip during intercourse and peelable afterwards to expose the adhesive seal and permit the proximal end to be pressed and joined together to prevent spillage from within the condom.

In another aspect of the present invention, the female condom device is disposed in a cup-like vending package, with the closed distal end of the condom disposed in the bottom of the cup portion and the proximal end rolled about the retaining ring. The broad tip of the applicator is disposed within the distal end of the condom, and the telescoping handle is collapsed to fit within the package. A top membrane seals the cup-like package to assure antiseptic conditions.

BRIEF DESCRIPTION OF THE DRAWINGS

FIG. 1 is an exploded view of the female condom and applicator of the present invention.

FIG. 2 is a schematic end view of the female condom of the present invention inserted in place.

FIG. 3 is a perspective view of a simplified form of the female condom of the present invention, shown with the tubular applicator inserted therein.

FIG. 4 is a perspective view of a further embodiment of the female condom of the present invention, including an expandable proximal end cap.

FIG. 5 is a partially cutaway perspective view of a further embodiment of the female condom, including an expandable sidewall having a resilient convex shape to aid in retention of the condom after insertion.

FIG. 6 is a perspective view of a further embodiment of the female condom, including an expandable sidewall having a compliant gel lining.

FIG. 7 is a perspective view of a further embodiment of the female condom, including a constricted proximal portion adapted to capture the male member after initiation of intercourse.

FIG. 8 is an end view of a further embodiment of the female condom, showing an adhesive seal for closing the proximal end of the condom after use.

FIG. 9 is an enlarged fragmentary cross-sectional view of the adhesive seal shown in FIG. 8.

FIG. 10 is a cross-sectional view of a further embodiment of the female condom, including a longitudinally extending pleat for diametrical expansion.

FIG. 11 is a cross-sectional end as in FIG. 10, showing the longitudinal pleat in an expanded disposition.

FIG. 12 is a cross-sectional end view of a further embodiment of the female condom, including a plurality of longitudinally extending pleats for diametrical expansion.

FIG. 13 is a perspective view of a further embodiment of the female condom, including a thickened distal end cap portion.

FIG. 14 is a perspective view of a further embodiment of the female condom, showing a spring-type diaphragm incorporated into the distal end of the condom.

FIGS. 15a and 15b are a sequence of enlarged, cross-sectional views of the retaining ring portion of the female condom, showing the unrolling of the condom from the retaining ring.

FIG. 16 is a perspective view of a preferred form of packaging for the female condom of the present invention, including the condom and an applicator received within a cup-like receptacle.

FIG. 17 is a top view of the package shown in FIG. 16.

FIG. 18 is a schematic view of the female condom and applicator, depicting the unrolling extension of the condom and the telescoping extension of the applicator.

FIG. 19 is an enlarged, cross-sectional view of the telescoping applicator of the present invention.

FIGS. 20a and 20b are a sequence of enlarged, cross-sectional views taken along line 20—20 of FIG. 19 and depicting the locking extension of the telescoping applicator handle.

DESCRIPTION OF THE PREFERRED EMBODIMENT

The present invention generally comprises a condom for use in preventing both contraception and transmission of venereal diseases. A salient feature of the invention is that it is designed to be used by a female prior to intercourse, rather than by the male, as is known in the prior art. With regard to FIG. 3, the basic configuration of the present invention includes a a condom 21 formed of a generally cylindrical tube 22. The tube 22 includes a distal end 23 having an integrally formed closure of generally hemispherical or smoothly rounded configuration, and a proximal end 24 that is open. A generally form-retaining applicator 26 is received within the condom 21 only for purposes of insertion of the condom into the vagina of the female. The applicator 26 in this embodiment comprises a solid rod or hollow tubular rod of polymer or plastic material having sufficient rigidity to be urged into the vaginal opening. The interior of the condom is provided with a lubricant to release the applicator rod and permit its withdrawal therefrom after insertion of the condom. The condom forms a closed lining of the vagina, with the proximal end of the condom extending outwardly of the vagina, to prevent epidermal genital contact during intercourse, and to prevent the release of semen within the vagina.

A salient feature of the female condom of the present invention is that it is a positive step that a woman may take prior to intercourse to assure contraception and prevent disease transmission, without requiring the participation or acquiescence of the male partner. Due to the fact that the female condom may be inserted long prior to intercourse, it does not necessarily comprise any interruption or interference with sexual intercourse.

A further embodiment 30 of the female condom, shown in FIG. 1, includes a generally cylindrical tube 28 having a closed, smoothly curved distal end 29. The proximal end portion 31 includes a bell-shaped portion flaring outwardly toward the proximal end and joined thereto to a semi-rigid, resilient retaining ring 32. The bell-shaped portion is larger in diameter than both the medial tube portion 28 and larger than the nominal vaginal opening. As the applicator 26 is used to insert the condom in the vagina, the bell-shaped portion 31 remains external to the vagina, forming a barrier between the male penis and the vaginal wall as well as the adjacent peroneal and vulvar areas 33, as depicted in FIG. 2. The extended barrier created by the portion 31 is particularly useful in preventing disease transmission. It should be noted that the ring 32 prevents collapse of the bell-shaped portion 31 and to maintain its protection.

Another embodiment 36 of the female condom, depicted in FIG. 4, includes the tubular portion 28, flared, bell-shaped portion 31, and retaining ring 32 described previously. It further includes a distal end having a thickened hemispherical portion 37 extending about the closed distal end. The portion 37 includes a plurality of fingers extending distally and spaced peripherally about the proximal end of the portion 28. The portion 37 and fingers 38 may be formed of a resilient, biologically compatible material, such as latex rubber or a synthetic equivalent. During insertion of the condom through the relatively narrow vaginal opening, the fingers 38 resiliently compress radially inwardly toward the axis of the tubular portion 28, thereby diminishing in diameter for purposes of insertion. After complete insertion of the portion 28 into the vagina, the fingers resiliently expand and reassert their original diameter. The increase in diameter retains the condom in place in the vagina, during and after intercourse. However, the condom can be removed by manually grasping the ring 32 and adjacent bell-shaped portion 31 and pulling the device from the vagina, the fingers 38 collapsing together during withdrawal.

With regard to FIG. 5, a further embodiment of the invention includes a female condom 41 having an outwardly flared, bell-shaped proximal portion 31 and retaining ring 32 as described previously. The tubular portion 43 of the condom is formed of a resilient membrane material having elastic memory, the portion 43 having a quiescent sidewall configuration of an prolate, elongated, closed curved structure having a rounded, blunt distal end 44 and a proximal end joined to the bell-shaped portion 31 by a diametrical constriction portion 42. It may be appreciated that during insertion of the condom by an applicator 26 or the like, the tensile force applied axially to the condom by the applicator causes the condom to elongate elastically and constrict diametrically. When the applicator is withdrawn, the elastic memory causes the portion 43 to reassert its quiescent, prolate form with the constricted diameter returning to normal and expanding against the vaginal wall to retain the condom within the vagina.

A further modification of the device of FIG. 5, shown in FIG. 6, comprises a female condom 48 having the same external configuration and components 31, 32, 42, 43, and 44 as the previous embodiment. The device 48 further includes an inner wall 46 having a generally cylindrical configuration, and a deformable gel layer 47 disposed between the two concentric walls 46 and 43. The shape of the device 48 creates a retaining effect within the vagina, as explained above in FIG. 5. Furthermore, after initiation of intercourse the insertion of the penis within the sidewall 46 causes some of the gel 47 to flow toward the proximal end of the device, creating a "plug" effect that further retains the female condom and prevents its accidental removal during intercourse.

The embodiment of the female condom shown in FIG. 7, unlike all the previous embodiments, is designed to be dislodged from the vagina by the penis during intercourse and to be subsequently retained on the penis similarly to a typical prior art male condom. It includes the retaining ring 32 and flared portion 31, as well as a narrow constriction 50 smaller in diameter than the constrictions 42 of the embodiments of FIGS. 5 and 6. Extending distally from the constriction 50 is an axially extending, cylindrical tubular membrane 52 having a closed, curved distal end 53. The condom 51 is easily inserted in the vagina using an applicator 26 or the like, the flared portion 31 protecting the outer genital area. After initiation of intercourse, the constriction 50 expands elastically to admit the penis, and thereafter contracts about the base of the penis and is retained thereat. The condom 51 is thereafter secured to the penis, and moves in concert therewith. Seminal fluid released within the condom is retained therein after completion of intercourse.

For those embodiments that are retained within the vagina during and after intercourse, the embodiment of FIGS. 8 and 9 is intended to seal the female condom after use and retain whatever fluids remain within it. A layer 56 of contact adhesive is applied to the inner peripheral surface of the retaining ring 32 of any of the embodiments described herein, and a peelable protective strip 57 is then applied to the adhesive. When intercourse is concluded, the strip 57 is peeled off, exposing the adhesive layer. The opposed portions of the ring 32 are then pressed together, sealing the proximal opening and preventing spillage of fluids within the condom during removal thereof. Alternately, after intercourse the proximal end may be either twisted or tied and knotted to seal the condom prior to removal.

A further modification of the present invention, shown in FIGS. 10–12, is directed toward enhancing the diametrical expansion of the female condom to prevent the condom from coupling to the male member and being pulled out of the vagina during intercourse. The generally cylindrical tubular portion 28 of the condom, as described previously, is provided with one pleat 61 (FIG. 10) or a plurality of pleats 61 (FIG. 12) extending longitudinally therealong. Each pleat comprises a pair of fold lines 62 extending longitudinally in mutual opposition, with a pair of flaps of overlapping condom sidewalls extending from each respective fold line, as best shown in FIG. 10. The sidewall portions involved in the pleat determine a diameter D of the condom, the diameter D being sufficiently small to facilitate insertion of the condom. After initiation of intercourse, if the diameter of the penis is greater than diameter D, the pleat (or pleats) will unfold, as shown in FIG. 11, to a dimension D+X, sufficient to accommodate the larger penis and assure that the condom will not engage and be retained on the penis. Thus the condom will remain in the vagina, to be removed manually after intercourse.

Another embodiment of the present invention, shown in FIG. 13, includes the tubular portion 28 and the flared portion 31 and retaining ring 32 described previously. The distal end of the portion 28 is closed by an expandable cap 64 that is formed with a wall thickness greater than the relatively thin wall of the tubular portion 28. The increased diameter and form-retaining nature of the thickened end portion 64 acts to anchor the condom in the vagina and prevent accidental withdrawel, and is easier to manufacture than the embodiment of FIG. 4, for example.

With regard to FIG. 14, a further embodiment of the present invention comprises a female condom having a proximal retaining ring 32 and a large diameter cylindrical proximal portion 66 designed to provide exterior protection from epidermal contact. The proximal portion 66 is joined to a medial cylindrical portion 67 of reduced diameter. At the distal end of the device, an arcing spring diaphragm 68 (known in the prior art for contraceptive purposes) is joined to the distal end of the portion 67. The diaphragm anchors the device within the vagina, the portion 67 lining the vaginal wall to prevent transmission of disease or passage of spermatozoa.

A significant aspect of the retaining ring 32 portion of several of the embodiments described above is that the ring 32 forms a base upon which the condom portion 31 or 66 may be rolled to reduce the length of the condom for purposes of packaging, as shown in FIG. 15b. Also, it may be appreciated that the condom can be unrolled from the retaining ring 32 to a length sufficient for the anatomy of the user (FIG. 15a), so that one size female condom may accomodate most users. Furthermore, the rolled up portion remaining external to the vagina is unnoticable, and the ability to take up surplus length at the exterior avoids awkward amounts of condom material in the female genital region.

With regard to FIGS. 16 and 17, one form of package suitable for the female condom comprises a cup-like receptacle 68 formed by vacuum forming or molding of impervious plastic material. A flange 69 extends from the upper edge of the receptacle 68, and a peelable, sealed top 70 is secured to the flange 69 to hermetically seal the receptacle and the condom 71 stored within. The condom 71 is rolled at its proximal end about the retaining ring 32 to foreshorten the condom and permit its fitting into the receptacle. In addition, an applicator 72 is received concentrically within the receptacle and within the distal end of the condom in the package. The applicator includes a broad distal tip 73 formed of expanded foam material or the like and impregnated with a lubricant, such as polydimethylsiloxane or the equivalent. Joined to the tip 73 and extending coaxially and distally therefrom is a telescoping handle 74. The handle comprises a plurality of tubular, nesting sections that are collapsed into a concentric configuration in the package 68.

As shown in FIG. 20a, each section 74a of the handle 74 includes a flange 76 extending radially at the distal end thereof, and an annular flange 77 spaced apart from the flange 76 to define an annular gap therebetween. The flange 77 includes a ramped distal surface. Each section 74b includes at its proximal end a flange 78 extending radially inwardly from the interior bore surface thereof and provided with a ramped surface 81. When the section 74b is pulled distally, as shown in FIG. 20b, the surface 81 of the flange 78 rides over the surface 79 of the flange 77 in snap action, the flange 78 being retained thereafter in the annular gap between the flanges 76 and 77. Thus mere manual tension applied to the distal end of the applicator 74 in the opened package 68 causes the handle to telescope outwardly from the package and form a rigid, elongated tubular assembly. Thereafter the female condom may be removed from the package, and the retaining ring may be unrolled to define a suitable length for the female condom, as shown in FIG. 18. The condom 71 is then inserted in the vagina, using the extended applicator, and the applicator is removed and discarded. It may be appreciated that the lubricant incorporated in the tip 73 remains within the condom to ease the passage of the penis therein. Furthermore, the insertion of the condom in the vagina prior to intercourse warms the condom to body temperature prior to coitus, so that the chilling effect of prior art male condoms is avoided.

It may be appreciated that there are various features described in the many embodiments of the present invention. It is within the scope of the invention to combine these features in various configurations as required, without departing from the intent or overall purpose of the invention.

It should be noted that the present invention has been described with regard to heterosexual intercourse; it may be appreciated that it can be used equally effectively in homosexual intercourse to prevent disease transmission.

I claim:

1. A female condom, comprising a hollow tubular member formed of a thin, pliant, web material having a continuous, curved sidewall disposed about a longitudinal axis and including proximal and distal ends, said distal end having an end closure formed integrally with said sidewall, said proximal end being open, and removable means for inserting said tubular member into the vagina with said distal, closed end extending innermost and said proximal, open end extending outward of the vagina, said removable means for inserting said tubular member comprising an applicator assembly, said applicator assembly including a distal tip portion dimensioned to engage the inner surface of said closed, distal end, and a tubular handle extending generally axially from said distal tip portion and distally therefrom, further including a cup-like sealed package for storing and protecting said condom and said applicator assembly, said applicator assembly being disposed with said distal tip portion and said tubular handle received concentrically within said hollow tubular member, wherein said proximal end of said hollow tubular member is rolled toroidally to foreshorten the length of said condom in said package, and said distal tip portion of said applicator includes means for storing and dispensing a lubricant substance to the interior surface of said hollow tubular member.

2. The female condom of claim 1, wherein said distal tip portion includes a resilient, porous portion impregnated with said lubricant substance.

3. A female condom, comprising a hollow tubular member formed of a thin, pliant, web material having a continuous, curved sidewall disposed about a longitudinal axis and including proximal and distal ends, said distal end having an end closure formed integrally with said sidewall, said proximal end being open, and removable means for inserting said tubular member into the vagina with said distal, closed end extending innermost and said proximal, open end extending outward of the vagina;

said removable means for inserting said tubular member comprising an applicator assembly, said applicator assembly including a distal tip portion dimensioned to engage and bear upon the inner surface of said closed, distal end, and a tubular handle extending generally axially from said distal tip portion and proximally therefrom;

said tubular handle including means for telescoping and elongating in the axial direction.

4. The female condom of claim 3, further including means secured to said proximal end for maintaining said proximal open.

5. The female condom of claim 4, wherein said means for maintaining said proximal end includes a retaining ring secured to proximal end, said retaining ring being form-retaining and resilient and having a diameter at least as great as the diameter of said hollow tubular member.

6. The female condom of claim 5, wherein said hollow tubular member includes a proximal end portion flaring outwardly toward said retaining ring, said retaining ring having a diameter greater than said diameter of said hollow tubular member.

7. The female condom of claim 6, wherein said proximal end portion is rolled about said retaining ring to decrease the length of said condom, and said retaining ring is sufficiently pliant so that said proximal end portion may be unrolled from said retaining ring to increase the length of said condom.

8. The female condom of claim 6, further including adhesive seal means secured to said retaining ring, said adhesive seal means including a strip of contact adhesive applied to said retaining ring and a peelable protective strip secured to said adhesive and selectively removable therefrom to expose said adhesive and permit adhesion and closure of said retaining ring and said proximal end.

9. The female condom of claim 3, further including adhesive seal means for closing the proximal end of said tubular member after use, said adhesive seal means including a strip of contact adhesive applied to the proximal end of said hollow tubular member, and a peelable protective strip secured to said adhesive and selectively removable therefrom to expose said adhesive and permit adhesion and closure of said proximal end.

10. The female condom of claim 3, further including a cup-like sealed package for storing and protecting said condom and said applicator assembly, said applicator assembly being disposed with said distal tip portion and said tubular handle received concentrically within said hollow tubular member.

11. The female condom of claim 10, wherein said proximal end of said hollow tubular member is rolled toroidally to foreshorten the length of said condom in said package.

12. The female condom of claim 11, wherein said tubular handle includes telescoping means for expanding in length from a collapsed configuration to an extended length configuration, said tubular handle being disposed in said collapsed configuration in said package, and means for locking said telescoping means in said extended length configuration.

13. The female condom of claim 21, further including a top panel secured to the open upper end of said cup-like package in hermetically sealed fashion, and means for releasably peeling said top panel from said package to remove said condom and applicator assembly.

14. A female condom, comprising a hollow tubular member formed of a thin, pliant, web material having a continuous, curved sidewall disposed about a longitudinal axis and including proximal and distal ends, said distal end having an end closure formed integrally with said sidewall, said proximal end being open, and removable means for inserting said tubular member into the vagina with said distal, closed end extending innermost and said proximal, open end extending outward of the vagina;

means at said distal end of said hollow tubular member for increasing the retention of said condom within the vagina, including a cap integrally formed at said distal end closure, said cap having a diameter greater than the diameter of said hollow tubular member; and a plurality of collapsible fingers extending proximally from said cap and joined to said hollow tubular member and spaced circumferentially thereabout, said fingers being adapted to collapse together in compression during insertion of said condom in the vagina and to expand resiliently against the vaginal wall to anchor said condom therein.

15. The female condom of claim 14, wherein said cap is provided with a wall thickness greater than the thickness of said sidewall of said hollow tubular member.

* * * * *